(12) United States Patent
Kan et al.

(10) Patent No.: US 10,930,394 B2
(45) Date of Patent: Feb. 23, 2021

(54) LIFESTYLE MANAGEMENT SUPPORTING APPARATUS AND LIFESTYLE MANAGEMENT SUPPORTING METHOD

(71) Applicants: OMRON Corporation, Kyoto (JP); OMRON HEALTHCARE Co., Ltd., Kyoto (JP); Kyushu University, National University Corporation, Fukuoka (JP)

(72) Inventors: Eriko Kan, Kyoto (JP); Mika Kijimuta, Kyoto (JP); Sho Nagayoshi, Kyoto (JP); Yoshinori Masaki, Fukuoka (JP)

(73) Assignees: Omron Corporation, Kyoto (JP); OMRON HEALTHCARE Co., Ltd., Kyoto (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 383 days.

(21) Appl. No.: 15/899,271

(22) Filed: Feb. 19, 2018

(65) Prior Publication Data
US 2018/0197434 A1    Jul. 12, 2018

Related U.S. Application Data

(63) Continuation of application No. PCT/JP2016/072887, filed on Aug. 4, 2016.

(30) Foreign Application Priority Data

Aug. 24, 2015 (JP) .............................. JP2015-165134

(51) Int. Cl.
*G16H 10/20* (2018.01)
*G16H 20/70* (2018.01)
(Continued)

(52) U.S. Cl.
CPC ......... *G16H 40/63* (2018.01); *A61B 5/02055* (2013.01); *A61B 5/165* (2013.01);
(Continued)

(58) Field of Classification Search
CPC ........ A61B 5/107; A61B 5/165; G16H 10/20; G16H 20/00; G16H 20/70; G09B 7/10
See application file for complete search history.

(56) References Cited

U.S. PATENT DOCUMENTS

| 9,307,914 B2 * | 4/2016 | Fahey ................. A61B 5/0002 |
| 2005/0216243 A1 * | 9/2005 | Graham ................. G16H 50/50 |
| | | 703/11 |

(Continued)

FOREIGN PATENT DOCUMENTS

| EP | 3007127 A1 | 4/2016 |
| JP | H11-149499 A | 6/1999 |

(Continued)

OTHER PUBLICATIONS

The Role of Expectancy and Self-Efficacy Beliefs, Pintrich and Schunk, 1996, all 19 pages are relevant, including Fig. 3.3 on p. 12.*

(Continued)

*Primary Examiner* — James S. McClellan
(74) *Attorney, Agent, or Firm* — Osha Bergman Watanabe & Burton LLP

(57) ABSTRACT

A lifestyle management supporting apparatus: acquires lifestyle-related information related to the lifestyle of a subject person; determines a psychological state index value which indicates a level of self-efficacy for the lifestyle improvement, based on the lifestyle-related information; determines a behavioral state index value which indicates a level of behavioral achievement for the lifestyle improvement, based on the lifestyle-related information; determines a type of the subject person by using a classification by axes of indexes (Continued)

including the psychological state index and the behavioral state index; and provides control unit providing support information conforming to the type of the subject person.

9 Claims, 9 Drawing Sheets

(51) Int. Cl.
| | |
|---|---|
| *G16H 20/00* | (2018.01) |
| *G09B 7/10* | (2006.01) |
| *G16H 40/63* | (2018.01) |
| *A61B 5/0205* | (2006.01) |
| *A61B 5/16* | (2006.01) |
| *A63B 24/00* | (2006.01) |
| *G09B 5/02* | (2006.01) |
| *G09B 19/00* | (2006.01) |
| *H04L 12/58* | (2006.01) |
| *A61B 5/021* | (2006.01) |
| *A61B 5/024* | (2006.01) |
| *A61B 5/11* | (2006.01) |
| *A61B 5/145* | (2006.01) |
| *A61B 5/00* | (2006.01) |

(52) U.S. Cl.
CPC ............ *A63B 24/0062* (2013.01); *G09B 5/02* (2013.01); *G09B 7/10* (2013.01); *G09B 19/00* (2013.01); *G09B 19/0092* (2013.01); *G16H 10/20* (2018.01); *G16H 20/00* (2018.01); *G16H 20/70* (2018.01); *H04L 51/046* (2013.01); *A61B 5/021* (2013.01); *A61B 5/024* (2013.01); *A61B 5/1118* (2013.01); *A61B 5/14532* (2013.01); *A61B 5/4812* (2013.01); *A61B 5/4869* (2013.01)

(56) References Cited

U.S. PATENT DOCUMENTS

2012/0150761 A1\* 6/2012 Ananian ............ G06Q 10/1053
705/321
2012/0302843 A1    11/2012 Otsubo et al.

FOREIGN PATENT DOCUMENTS

| JP | 2000-305988 A | 11/2000 |
|---|---|---|
| JP | 2001-022837 A | 1/2001 |
| JP | 2011-107978 A | 6/2011 |
| JP | 2012-113393 A | 6/2012 |
| JP | 2012-128798 A | 7/2012 |
| JP | 2015-026233 A | 2/2015 |
| WO | 2014/188657 A1 | 11/2014 |

OTHER PUBLICATIONS

Extended Search Report issued in European application No. 16839044.1, dated Nov. 22, 2018 (10 pages).
International Search Report issued in Application No. PCT/JP2016/072887, dated Sep. 20, 2016 (2 pages).
Written Opinion issued in Application No. PCT/JP2016/072887, dated Sep. 20, 2016 (4 pages).

\* cited by examiner

| INFO. SOURCE / TYPE | ACHIEVEMENT | SUBSTITUTE | VERVBAL | EMOTIONAL | FREQ. |
|---|---|---|---|---|---|
| TYPE 1 | 0.5 | 0.2 | 0.2 | 0.1 | LOW |
| TYPE 2 | 0.3 | 0.2 | 0.3 | 0.2 | HIGH |
| TYPE 3 | 0.2 | 0.3 | 0.2 | 0.3 | MID |
| TYPE 4 | 0.3 | 0.3 | 0.2 | 0.2 | HIGH |

FIG.5A
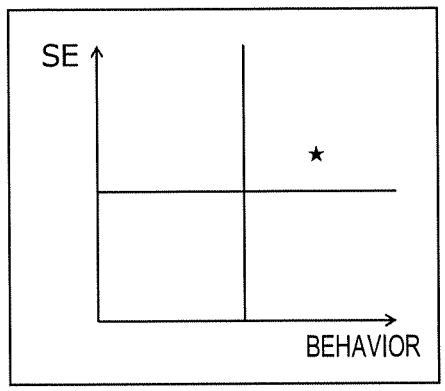
FIG.5B
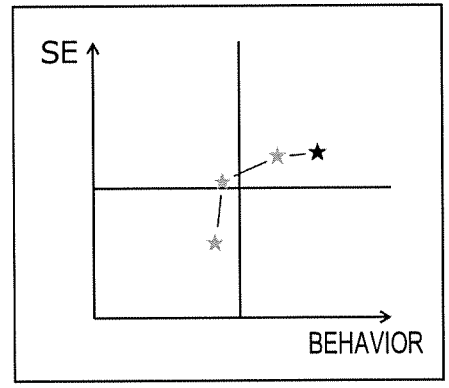
FIG.5C
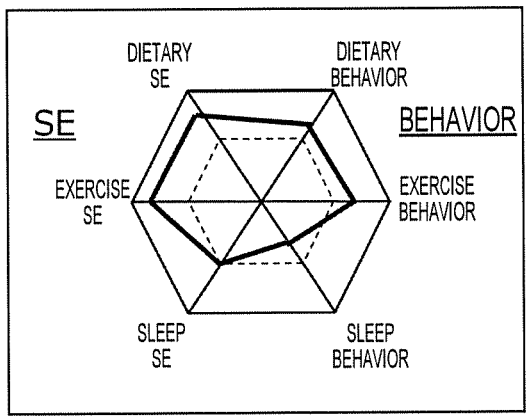
FIG.5D
MR. OO IS TYPE 1.
YOU SEEM TO HAVE TENDENCY TO ...

FIG.6

| SUB-JECT | | RULE | INFO. SOURCE | MESSAGE |
|---|---|---|---|---|
| EXERCISE | 1 | NUMBER OF CONTINUOUS WEEKS WHEN TARGET NUMBER OF STEPS WAS ACHIEVED ≥ th | ACHIEVEMENT | MR. O CLEARED TARGET NUMBER OF STEPS CONTINUOUSLY FOR th-WEEKS !! KEEP UP AND IMPROVE THE RECORD ! |
| | 2 | AVERAGE NUMBER OF STEPS IN MOST RECENT ONE WEEK < NUMBER OF STEPS OF SAME AGE GROUP | SUBSTITUTE | THE AVERAGE NUMBER OF STEPS OF MR. O IS LOWER THAN XX STEPS OF THE SAME AGE GROUP. FIRST TRY TO WALK HOME FROM THE STATION, TARGETING INCREASING 500 TO 1000 STEPS OR MORE. MANY TRY THIS METHOD. |
| | 3 | NUMBER OF WEEKS IN WHICH TARGET NUMBER OF STEPS WAS ACHIEVED ≥ th & WEIGHT CHANGE AMOUNT ≥ -0.1 | VERBAL | THE TARGET NUMBER OF STEPS HAS BEEN CLEARED FOR LAST th-WEEKS. WEIGHT DOES NOT CHANGE, BUT DON'T BE DISCOURAGED. RESULTS ARE SEEN LATER. DON'T GET FRUSTRATED. |
| | 4 | TOTAL WALKING DISTANCE FROM START ≥ 100 km | ACHIEVEMENT | THE WALKING DISTANCE SINCE PROGRAM START EXCEEDED 100 KM. THIS IS THE DISTANCE FROM YOUR HOME TO XX. AMAZING !! CONTINUING EVERY DAY IS VERY IMPORTANT. |
| | 5 | ... | ... | ... |

FIG.9

| FOUR ELEMENTS TO IMPROVE SE | | EXAMPLE | EXAMPLE OF ACQUIRED RESPONSE |
|---|---|---|---|
| 1 | ACHIEVEMENT EXPERIENCE | NUMBER OF STEPS INCREASED BY XX STEPS COMPARED TO LAST WEEK. | I LIKE IT ! / NOT SO SURE. |
| 2 | SUBSTITUTE EXPERIENCE | A PERSON ACHIEVED THE SAME NUMBER OF STEPS AS MR. O LOST AVERAGE XX kg AFTER 3 MONTHS. | OK ! / NOT SO SURE. |
| 3 | VERBAL PERSUASION | PUBLIC HEALTH NURSE STATES: "YOU WALK EVERY DAY, EVEN IN RAIN. KEEP IT UP, AND BREAK THE RECORD" | OK ! / NOT SO SURE. |
| 4 | PHYSIOLOGICAL/ EMOTIONAL UPLIFT | ISN'T IT EASIER NOW TO WALK UP AND DOWN STEPS? | YES ! / NOT SO SURE. |

FIG.10

IN THE CASE OF TYPE 1

| | ACHIEVEMENT | SUBSTITUTE | VERBAL | EMOTIONAL |
|---|---|---|---|---|
| DEFAULT PRIORITY LEVEL | 0.5 | 0.2 | 0.2 | 0.1 |
| RESPONSE RATE | 0.9 | 0.4 | 0.8 | 0.3 |
| CHANGED PRIORITY LEVEL | 0.53 | 0.18 | 0.22 | 0.07 |

LIFESTYLE MANAGEMENT SUPPORTING APPARATUS AND LIFESTYLE MANAGEMENT SUPPORTING METHOD

BACKGROUND OF THE INVENTION

Field of the Invention

The present invention relates to a technique to support improvement in the lifestyle of a subject person.

Description of the Related Art

To prevent lifestyle-related diseases, such as diabetes, it is known that an improvement in lifestyle, including diet, exercise and sleep, is effective. However, changing a long habitual lifestyle and maintaining a new lifestyle is not easy. Therefore in Japan, efforts to support an improvement in the lifestyle of a subject person are advancing by the discovery of lifestyle problems, setting attainable behavioral goals, and following up improvement states through the health guidance of a physician and public health nurse. Further, computer systems, to evaluate the improvement state of a lifestyle and provide advice, have lately been proposed in order to simplify self care (self management) by the subject person himself.

For example, PTL 1 proposes a system which determines a psychological state (e.g. willingness, confidence, expectation) of a subject person based on a questionnaire filled out by the subject person, and provides advice in accordance with a scenario that matches the psychological state of the subject person.

PTL 1: Japanese Patent Application Publication No. 2001-22837

SUMMARY OF THE INVENTION

However, with the study of prior art, it became clear that considering the psychological state of the subject person alone in some cases cannot provide effective advice. This is because the personality and the behavior characteristics of individuals vary, and the psychological state (e.g. willingness, confidence) and the actual behavior (how to approach an improvement in lifestyle) are not always linked. For example, some individuals constantly and seriously work on lifestyle targets each day, while others tend to delay in taking action and tend to be lazy, even if they all have willingness and confidence. Therefore it is desirable to change the content of advice and the way of providing advice depending on whether the subject person is the former type or the latter type, even if the psychological state is not different.

With the foregoing in view, it is an object of the present invention to provide a technique to accurately know the state of the subject person for lifestyle improvement, and enable a more effective lifestyle improvement support.

To achieve this object, a lifestyle management supporting apparatus according to the present invention is an apparatus for providing support information to support the lifestyle improvement of a subject person, this apparatus having: a lifestyle-related information acquiring unit configured to acquire lifestyle-related information which is related to the lifestyle of the subject person; a psychological state evaluating unit configured to determine a value of a psychological state index which indicates a level of self-efficacy for the lifestyle improvement, based on the lifestyle-related information of the subject person; a behavioral state evaluating unit configured to determine a value of a behavioral state index which indicates a level of behavioral achievement for the lifestyle improvement, based on the lifestyle-related information of the subject person; a type determining unit configured to determine a type of the subject person, based on the value of the psychological state index and the value of the behavioral state index of the subject person by using a classification by a plurality of axes of indices including the psychological state index and the behavioral state index; and an information providing control unit configured to provide support information matching the type of the subject person.

According to this configuration, a type of the subject person, in terms of the way of working on lifestyle improvement, can be determined based on the psychological state (level of self-efficacy) and the behavioral state (level of behavioral achievement) of the subject person, and support information matching the type of the subject person can be provided. Therefore compared with conventional methods which consider only the psychological state, support information more suitable for the personality and behavioral characteristics of the subject person can be provided.

It is preferable that the lifestyle management supporting apparatus further includes a message storing unit configured to store in advance a plurality of messages, which respectively correspond to achievement experience, substitute experience, verbal persuasion and physiological/emotional uplift, which are the four information sources that influence self-efficacy. In this case, it is preferable that the information providing control unit has a function to provide a message, which is read from the message storing unit, as the support information, and when a message to be provided to the subject person is selected from the plurality of messages, the information providing control unit changes priority in selection of a message corresponding to the information source, depending on the type of the subject person.

It is known that the four information sources (achievement experience, substitute experience, verbal persuasion, physiological/emotional uplift) influence acquiring and improving self-efficacy. The intensity of this influence, however, is not the same for everyone, because an effective information source differs depending on the personality and behavioral characteristics of an individual. According to the configuration of the present invention, it can be controlled such that an information source matching the type of the subject person can be provided with priority, hence the self-efficacy of the subject person can be effectively improved, and the change of behavior in lifestyle improvement and continuation thereof may be promoted.

It is preferable that the information providing control unit includes a table in which relative priority levels, among the four information sources, are defined for each type, and when a message to provide to the subject person is selected from the plurality of messages, the information providing control unit selects an information source based on probability in accordance with the relative priority level corresponding to the type of the subject person, and then selects a message corresponding to the selected information source.

By using this table and applying the selection logic, control of the priority levels in accordance with the type can be easily implemented. Furthermore, the information source to be selected is determined based on probability, hence selecting the same type of information source at high frequency can be prevented probabilistically.

It is preferable that the information providing control unit has a function to acquire the result of response from the subject person when a message is provided, and record for each information source the response rate, which is a ratio of the messages of which result of response is positive, with respect to the total number of provided messages, and the information providing control unit changes the relative priority levels among the four information sources, based on the response rate of each information source, so that the priority level of the information source having a relatively high response rate becomes high.

According to this configuration, the type of the information source to which the subject person responds positively (that is, the influence on improvement of the self-efficacy of the subject person may be high) can be learned, and the ratio of providing messages corresponding to this information source can be increased automatically. As a result, effective support information, matching the personality of the subject person more so, may be provided.

It is preferable that the type determining unit classifies subject persons into four types (type 1 having high self-efficacy and high behavioral achievement, type 2 having low self-efficacy and high behavioral achievement, type 3 having high self-efficacy and low behavioral achievement, and type 4 having low self-efficacy and low behavioral achievement) by using the two axes of indices (the psychological state index and the behavioral state index).

By using such a simple 2 axes-4 quadrant matrix, types can be simply and easily classified based on the psychological state and the behavioral state. Type 1 is a type who can self manage well. For a type 1 person, it is preferable to select a message corresponding to "achievement experience" with priority over messages corresponding to other information sources. Type 2 is a type who is vulnerable to interruptions (easily influenced by circumstances). For a type 2 person, it is preferable to select a message corresponding to "achievement experience" and a message corresponding to "verbal persuasion" with priority over messages corresponding to other information sources. Type 3 is a type who is insensitive to an impending crisis and easily becomes lazy. For a type 3 person, it is preferable to select a message corresponding to "substitute experience" and a message corresponding to "physiological/emotional uplift" with priority over message corresponding to other information sources. Type 4 is a type who has no confidence and easily uses excuses. For a type 4 person, it is preferable to select a message corresponding to "achievement experience" and a message corresponding to "substitute experience" with priority over messages corresponding to the other information sources.

It is preferable that the information providing control unit changes the frequency to provide the support information to the subject person, depending on the type of the subject person. According to this configuration, the support information can be provided at a frequency that is suitable for the psychological state and the behavioral state of the subject person, hence a greater effect can be expected. For example, it is more effective to provide information more frequently to a person who has low self-efficacy, but providing information too frequently to a person who has high self-efficacy may have an adverse effect. Therefore if the behavioral achievement is the same among the types, the frequency of providing information should be set higher as the subject person has a lower self-efficacy. To a person having high behavioral achievement, the frequency of providing information can be low. This means that if self-efficacy is the same among the types, the frequency should be set higher as the subject person has a lower behavioral achievement.

It is preferable that as the support information, the information providing control unit has a function to present the type of the subject person determined by the type determining unit. Even presenting the type determination result alone is useful, because the subject person can be made aware of their type, and the public health nurse can use this information as reference information.

A lifestyle management supporting apparatus according to another aspect of the present invention is a lifestyle management supporting apparatus for providing support information to support lifestyle improvement of a subject person, having: a lifestyle-related information acquiring unit configured to acquire lifestyle-related information which is related to the lifestyle of the subject person; a state evaluating unit configured to determine a plurality of values of state indices for evaluating the state of the subject person in terms of lifestyle improvement based on the lifestyle-related information of the subject person; a type determining unit configured to determine a type of the subject person based on the values of the plurality of state indices of the subject person, using a classification by a plurality of axes of state indices; and an information providing control unit configured to provide support information matching the type of the subject person.

According to this configuration, a type of the subject person to work on the lifestyle improvement can be determined based on a plurality of state indices, and support information matching the type of the subject person can be provided. Therefore compared with conventional methods which consider only the psychological state, support information that is more suitable for the personality and behavioral characteristics of the subject person can be provided.

Here "lifestyle-related information" can be any information if the information is directly or indirectly related to the lifestyle of the subject person, and may be information that is manually inputted or information that is uploaded from other devices. For example, a questionnaire on lifestyle may be filled out by the subject person, and the response data may be acquired as a part of the lifestyle-related information. Or the behavior and biological information of the subject person may be measured by various measuring devices, and this measurement data may be acquired as a part of the lifestyle-related information. To more accurately understand the state of the subject person, it is preferable to acquire a plurality of types of lifestyle-related information, and to acquire time-series data during a certain period that is as current as possible (especially in the case of measurement data).

The present invention can also be regarded as a lifestyle management supporting apparatus which includes at least a part of the above mentioned configuration and functions. The present invention can also be regarded as a lifestyle management supporting method that includes at least a part of the above mentioned processing, or a program that causes a computer to execute such a method, or a non-transitory computer-readable storage medium which stores such a program. The present invention may be configured by combining each of the above mentioned configurations and processing within a scope of not causing technical inconstancy.

According to the present invention, the state of the subject person in lifestyle management can be more accurately understood, and a more effective lifestyle improvement support can be provided.

BRIEF DESCRIPTION OF THE DRAWINGS

FIG. 5A to FIG. 5D are examples of a type confirming screen;

FIG. 6 is an example of a message table;

FIG. 9 is an example of the messages and the response acquiring buttons; and

FIG. 10 is an example of the response rates and the updated priority levels.

DESCRIPTION OF THE EMBODIMENTS

Preferred embodiments of the present invention will now be described in detail with reference to the drawings.

(General Configuration of System)

Figure 1:
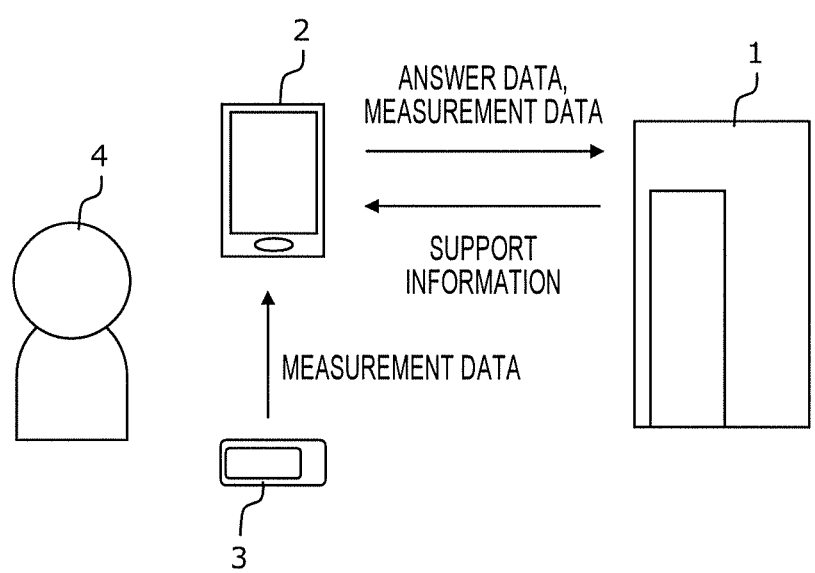
FIG. 1 is a schematic diagram depicting a general configuration of a lifestyle management supporting system according to an embodiment of the present invention.

FIG. 1 is a schematic diagram depicting a lifestyle management supporting system according to an embodiment of the present invention (hereafter may also be called "this system"). This system is a system for supporting a person 4 who works on the lifestyle improvement (hereafter called a "subject person"), and is constituted mainly by a lifestyle management supporting apparatus 1, a terminal device 2, and a measuring device 3.

The terminal device 2 is a terminal operated by the subject person 4, and has an interface (e.g. touch panel, keyboard, display) to input/output information for the subject person 4, and a communication function to communicate data between the lifestyle management supporting apparatus 1 and a measuring device 3. The data communication system can be such a system as wireless LAN, USB communication, NFC communication and Bluetooth®. For the terminal device 2, a smartphone, a tablet terminal, a personal computer or the like can be used. The terminal device 2 however is not limited to these devices, but may be a dedicated terminal. The measuring device 3 may also function as the terminal device 2.

The measuring device 3 is a device to measure behavioral or biological information of the subject person 4. A device which measures behavior is, for example: a pedometer which measures a number of steps and walking time; an activity amount meter which measures physical activity amount and exercise intensity; a sleep sensor which measures the sleeping state and sleeping time; a calorie mater which calculates calories of a meal; and a camera which photographs a meal (image recording). A device which measures biological information is, for example: a weight and body composition meter which measures the weight, body composition (body fat percentage, muscle mass), basal metabolism, BMI and the like; an adipometer which measures subcutaneous fat thickness; a blood sugar meter which measures the blood sugar level; a sphygmomanometer which measures blood pressure and pulse rate; a clinical thermometer which measures body temperature; and a heart rate meter which measures heart rate or the like. In FIG. 1, only one measuring device 3 is illustrated, but a plurality of types of measuring devices 3 may be disposed. The measurement data acquired by the measuring device 3 is transmitted to the lifestyle management supporting apparatus 1 via the terminal device 2, and is used to analyze the psychological state and the behavioral state of the subject person 4, which will be described later.

The lifestyle management supporting apparatus 1 is an apparatus that provides various functions and services to support the lifestyle improvement of the subject person 4. The functions and services that are provided are, for example: recording health diagnosis and health guidance; creating lifestyle improvement program (setting behavioral goals and schedule); displaying recorded/transition graph of measurement data of behavioral/biological information; and providing support information to the subject person 4. In the following, provisions of the support information, which are functions unique to this embodiment, will primarily be described, and the description of other functions will be omitted.

(Configuration of Lifestyle Management Supporting Apparatus)

Figure 2:
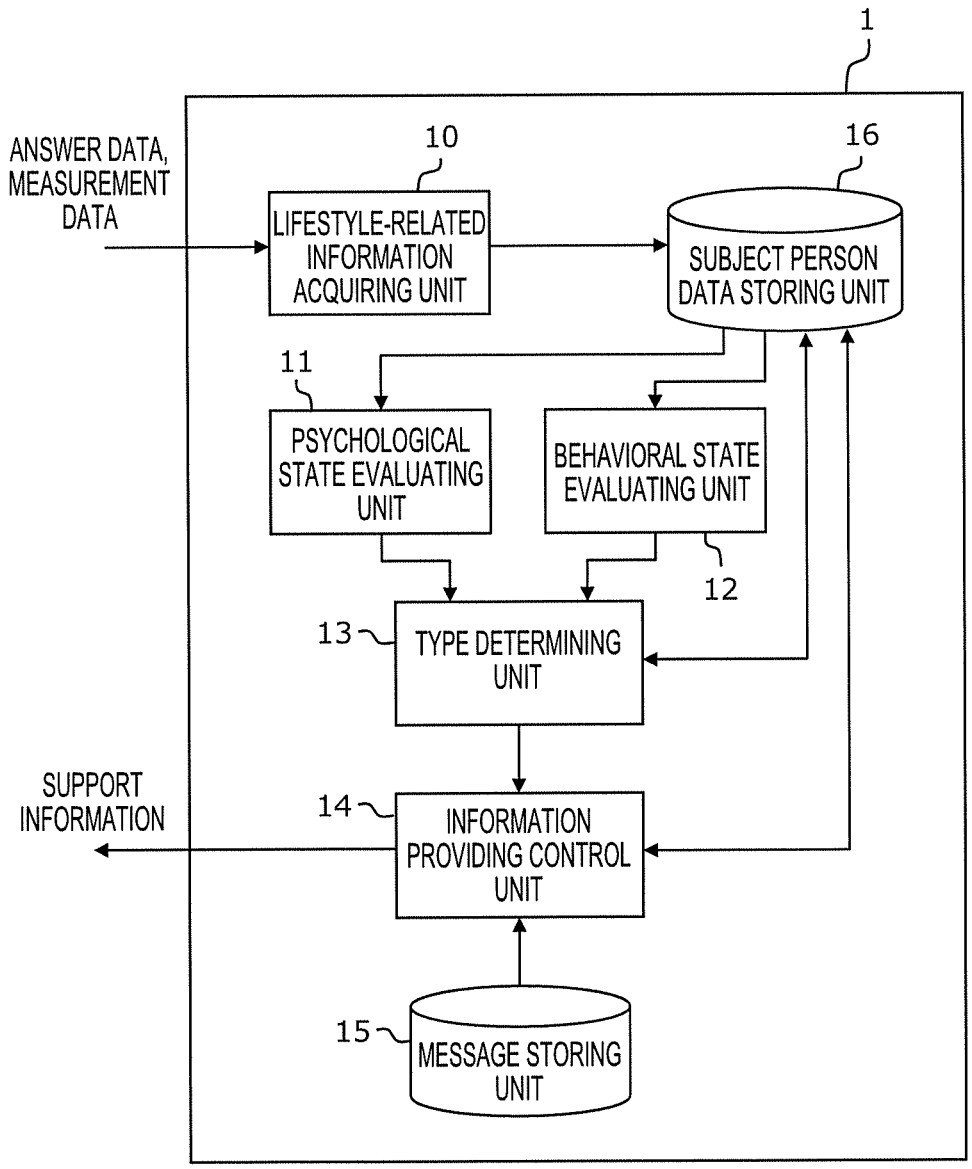
FIG. 2 is a schematic block diagram depicting a functional configuration of the lifestyle management supporting apparatus.

FIG. 2 is a schematic block diagram depicting the functional configuration of the lifestyle management supporting apparatus 1. As the functions related to the support information provisions, the lifestyle management supporting apparatus 1 has: a lifestyle-related information acquiring unit 10, a psychological state evaluating unit 11, a behavioral state evaluating unit 12, a type determining unit 13, an information providing control unit 14, a message storing unit 15, and a subject person data storing unit 16.

The lifestyle-related information acquiring unit 10 has a function to acquire information related to the lifestyle of the subject person 4 (called "lifestyle-related information") from the terminal device 2 or the like. In this embodiment, the response data to the questionnaire filled out by the subject person 4 and the measurement data acquired by the measuring device 3 are used as the lifestyle-related information. The psychological state evaluating unit 11 has a function to evaluate the psychological state of the subject person 4 based on the lifestyle-related information, and the behavioral state evaluating unit 12 has a function to evaluate the behavioral state of the subject person 4 based on the lifestyle-related information. The type determining unit 13 has a function to determine a type of the subject person 4 in terms of the way they work on the lifestyle improvement based on the psychological state and the behavioral state. The information providing control unit 14 has a function to provide the support information matching the type of the subject person 4, and the message storing unit 15 is a data base that stores, in advance, message which are provided as the support information. The subject person data storing unit 16 is a data base that stores the personal information of the subject person (e.g. ID, name, gender, age, height, weight, mail address), information related to lifestyle improvement (e.g. the behavioral plan and goal, the type of working on the lifestyle improvement), response data to the questionnaire, measurement data acquired by the measuring device 3 and the like. Details on these functions will be described later.

The lifestyle management supporting apparatus 1 of this embodiment can be configured using a general purpose computer, constituted by a CPU (central processing unit), memory, hard disk, communication device, input/output I/F and the like. Various functions depicted in FIG. 2 are implemented by the CPU reading and executing the required programs. In the case when the lifestyle management supporting apparatus 1 provides the support information providing service to many subject persons 4, the lifestyle management supporting apparatus 1 may be constituted using a computer server (e.g. cloud server), so that the service can be provided via Internet or the like. In the case when the lifestyle management supporting apparatus 1 is provided locally non-Internet, the lifestyle management supporting apparatus 1 may be constructed using an application program running on a personal computer or smartphone. In this case, the terminal device 2 is unnecessary, since the subject person 4 directly operates the lifestyle management supporting apparatus 1.

(Operation of Lifestyle Management Supporting Apparatus)

(1) User Registration

A person who is interested in using this system accesses a registration web page of the lifestyle management supporting apparatus 1 using the terminal device 2, and performs user registration by inputting necessary information, such as name, gender, age, height, weight and mail address. When the user registration completes, the subject person ID is assigned. Then the subject person 4 logs in to the lifestyle management supporting apparatus 1 using the assigned ID, enters the lifestyle improvement program, and sets a behavioral plan and goal, for example. A specific example could be losing 5 kg of weight in six months, walking at least 10,000 steps a day, and maintaining a caloric intake of a maximum 2500 kcal per day. The information that is inputted and set here is registered in the subject person data storing unit 16.

(2) Acquiring Measurement Data

When the subject person 4 measures their own behavioral or biological information using the measuring device 3, this measurement result is recorded in an internal memory of the measuring device 3, along with the measurement date and time. This measurement data is transmitted from the measuring device 3 to the terminal device 2 automatically, or according to the operation by the subject person 4. If the measuring device 3 has no communication function, the subject person 4 may manually input the measurement result, acquired by the measuring device 3 and the measurement date and time, to the terminal device 2.

The terminal device 2 attaches the user ID to the measurement data, and transmits this data to the lifestyle management supporting apparatus 1. When the measurement data is received via a network, the lifestyle-related information acquiring unit 10 of the lifestyle management supporting apparatus 1 determines the subject person 4 to whom this data belongs, based on the user ID, and stores this measurement data in the subject person data storing unit 16. Because of this structure, the measurement data of the subject person 4 is stored in a time-series.

(3) Conducting Questionnaire

The lifestyle-related information acquiring unit 10 can conduct a questionnaire on the lifestyle with the subject person 4. The questionnaire may be filled out at user registration, or may be filled out periodically at predetermined intervals after the system starts up, or may be filled out at a timing desired by the subject person 4.

For example, the lifestyle-related information acquiring unit 10 distributes a Web-based questionnaire or questionnaire application to the terminal device 2. The subject person 4 inputs responses to the questions on the screen of the terminal device 2. The response may be inputted by the subject person, or may be inputted by a third party (e.g. public health nurse).

The questions are set in accordance with the purpose of the questionnaire. If the purpose is to know self-efficacy in terms of exercise, possible questions may be, for example, Can you exercise even when tired?

Can you exercise even when busy?

And if the purpose is to know self-efficacy in terms of diet, possible questions may be, for example, Can you control diet on holidays?

Can you control eating and drinking at dinner parties and drinking parties?

A survey with a questionnaire may be conducted on whether behavioral goals on diet, exercise and sleep were achieved, and the degree to which the behavioral goals were achieved to date, asking, for example, Did you achieve the target 10,000 steps today?

Did you have a second helping at dinner?

Were there at least four days last week when the goal was achieved?

As for answers in the questionnaire, not only can a choice of YES/NO be input, but the content of the executed behavior (e.g. number of steps, consumed calories) may be input as well.

The terminal device 2 attaches the user ID to the response data of the questionnaire, and transmits this data to the lifestyle management supporting apparatus 1. When the response data is received via a network, the lifestyle-related information acquiring unit 10 determines the identity of the subject person 4 related to this data based on the user ID, and stores this response data in the subject person data storing unit 16. Because of this structure, the questionnaire result from the subject person 4 can be collected.

(4) Type Classification of Subject Person

In this system, "self-efficacy" is used as an index to evaluate the psychological state of the subject person 4. Self-efficacy, a concept advocated by psychologist Albert Bandura, refers to "a conviction or prospect on how well a required behavior to generate a certain result" can be implemented. Individuals control their ideas, emotions and behavior of their self through self-efficacy. In medical fields, self-efficacy is recognized as a concept to effectively manage behavior change in order to improve lifestyle, and it is believed that considering a way to improve the self-efficacy of the subject person 4 is very effective to improve the motivation of the person, and to change and sustain the behavior of that person.

According to Albert Bandura, self-efficacy is influenced by four information sources: "achievement experience", "substitute experience", "verbal persuasion", and "physiological/emotional uplift". "Achievement experience" refers to the success experience or failure experience in the past caused by performing a particular behavior. The achievement experience is a most powerful and most effective information source since information on the degree of accomplishment is directly provided. "Substitute experience" refers to a substitute experience by observing the state of success or failure of other individuals. "Verbal persuasion" refers to a teaching or confirmation by others to provide confidence of an accomplishment. By being influenced through the language of others, a person can be made aware and receive confidence that they have a certain capability. "Physiological/emotional uplift" is the information generated by partially sensing a physical capability, strength, function and the like via each part of the body, and judging this information. This means that the senses of the body of this person caused by performing a certain behavior become the information sources. For example, if this behavior is physical activity or exercise, the sensation of cardiopulmonary functions and the muscle senses can be major information sources.

In this way, the four information sources (achievement experience, substitute experience, verbal persuasion, physiological/emotional uplift) influence the acquisition and improvement of self-efficacy. However, it has become clear that the influence levels of these four information sources are not the same for every one, since effective information sources differ depending on the personal and behavioral characteristics of an individual. For example, even among individuals who have high self-efficacy and high willingness and confidence, some individuals are types that seriously work on the lifestyle improvement each day, and others are types that are insensitive to an impending crisis and do not take action easily. In the case of the former type, providing the achievement experience is effective as the information source, but in the case of the latter type, the substitute experience may be more effective than the achievement experience.

Therefore in this system, the types who work on the lifestyle improvement are classified based on the psychological state (level of self-efficacy) and the behavioral state (level of behavioral achievement), and the priority levels of the information sources to be provided are controlled in accordance with the type of the subject person 4.

Figures 3A, 3B:
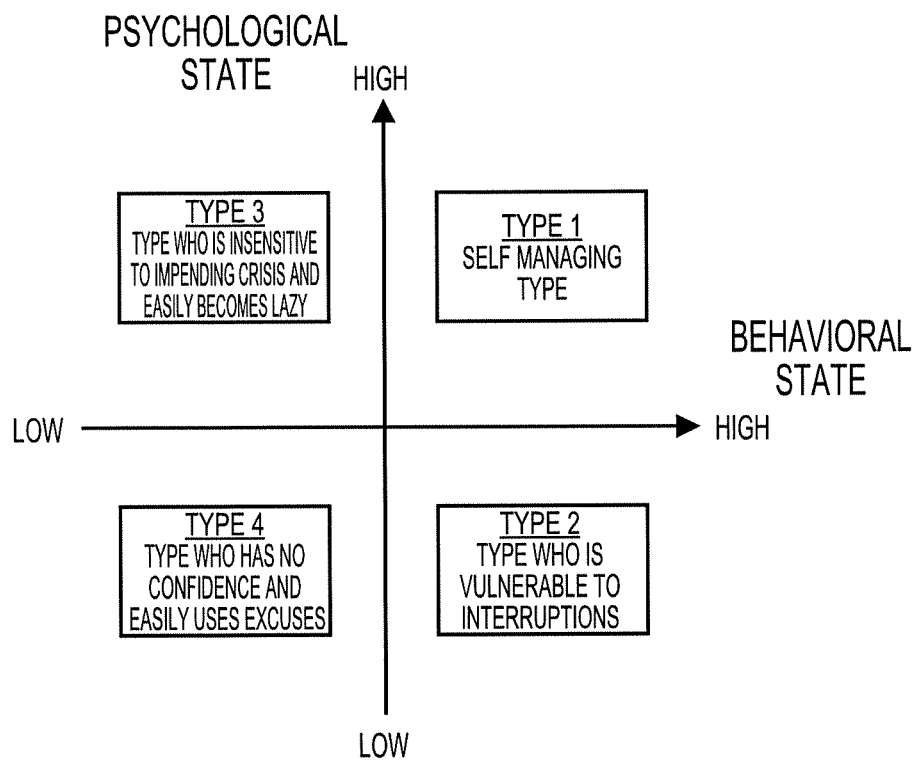
FIG. 3A is an example of the classification types regarding how to work on the lifestyle improvement.
FIG. 3B is an example of an information source priority table.

FIG. 3A is an example when the ways of working on the lifestyle improvement are classified into four types, using two index axes of the psychological state and the behavioral state. The feature of each type follows.

Type 1 (self managing type) is a type who has both high self-efficacy and high behavioral achievement, and who can manage themselves very well. For the type 1 person, it is effective to set the ratio of the achievement experience high, so as to "intensify the self analyzing capability by providing the success/failure results which lead to awareness". The frequency of providing information may be low, since the subject person of this type has the ability to manage themselves.

Type 2 (type who is vulnerable to interruptions) is a type who has high behavioral achievement but low self-efficacy, and who is easily influenced by the surrounding situation (e.g. overeating at a drinking party). For the type 2 person, it is effective to set the ratios of the achievement experience and the verbal persuasion high, so as to "praise the appropriate handling of interruptions (e.g. drinking party), to give confidence, and increase the willingness to deal with interruptions". In order to improve self-efficacy, it is better to provide information frequently.

Type 3 (type who is insensitive to impending crisis, and easily becomes lazy) is a type who has high self-efficacy, but who has low behavioral achievement. The type 3 person is insensitive to an impending crisis, takes a long time to take action, and easily becomes lazy. For the type 3 person, it is effective to set the substitute experience and the emotional uplift to high, so as to "provide a sense of crisis in future/change the point of view on being slack". The frequency of providing the information can be slightly low, and may be adjusted depending on the time and the situation.

Type 4 (type who has no confidence, and easily uses excuses) is a type who has both low self-efficacy and low behavioral achievement. The type 4 person has no confidence to improve lifestyle. For the type 4 person, it is effective to set the achievement experience and the substitute experience high, so as to "present a success example, and make the person aware that they too can achieve the same". The frequency of providing information can be high in order to improve the self-efficacy.

The type may be classified in terms of lifestyle improvement in general, or classified in terms of an individual lifestyle. In the latter, classification can be based on the "types of the way of working to improve dietary habits", "types of the way to working to improve exercise habits", and "types of the way of working to improve sleep habits". Lifestyle may be further subdivided.

FIG. 3B is an example of an information source priority table, which is set based on the characteristics of each type. The information priority table is a table in which a relative priority level among the four information sources is defined for each type. For example, in the case of type 1, the achievement experience is set to 0.5, the substitute experience to 0.2, the verbal persuasion to 0.2, and physiological/emotional uplift to 0.1. The value of each priority level indicates the probability that each information source is selected (provided). The table in FIG. 3B is merely an example, and the value of each priority level can be appropriately set in accordance with the logic of the information providing control unit 14, which refers to the background information (prior information) of each type and this table.

Figure 4:
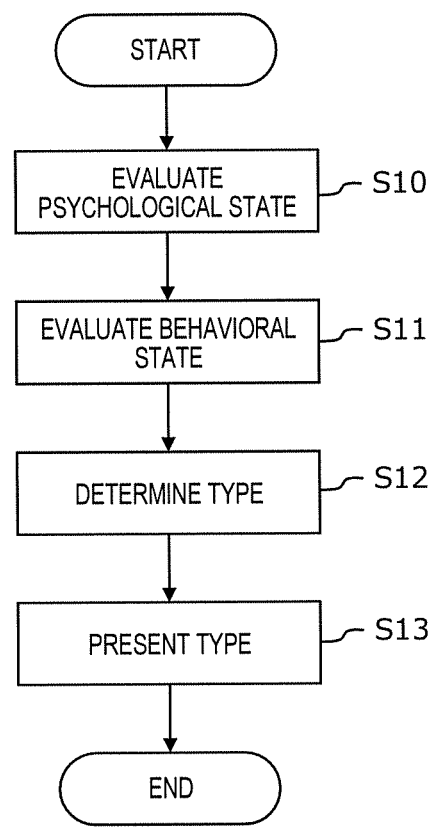
FIG. 4 is a flow chart of the type determination processing.

Processing of determining the type of the subject person 4 will be described next with reference to the flow chart in FIG. 4.

In step S10, the psychological state evaluating unit 11 reads the necessary data from the lifestyle-related information of the subject person 4 stored in the subject person data storing unit 16, and evaluates the level of the self-efficacy of the subject person 4 by analyzing this data. The state index, to indicate the level of self-efficacy (called "psychological state index"), can be designed in accordance with the type of the lifestyle-related information to be used, the purpose of the type classification and the like.

For example, in the case of using the above mentioned response data of the questionnaire on self-efficacy, points are assigned to each question in advance. Then the psychological state evaluating unit 11 determines the total points of the response data of the subject person 4, and regards this total score as the value of the psychological state index. Alternatively, the psychological state evaluating unit 11 may regard the measurement frequency, number of times of measurement, dispersion of measurement time or the like in the measurement data of the subject person 4, as the psychological state index. This is because as self-efficacy becomes higher, such a tendency as measuring weight more frequently or measuring weight at the same time each day appears. Needless to say, a plurality of indices may be combined, or an index determined from the response data of the questioner and an index determined from the measurement data may be combined. In this case, the value of the psychological state index may be calculated from a plurality of indices using an operation to determine an average, a sum total, a weight average, the weighted sum or the like, and a function.

In step S11, the behavioral state evaluating unit 12 reads the necessary data from the lifestyle-related information of the subject person 4 stored in the subject person data storing unit 16, and evaluates the level of the behavioral achievement of the subject person 4 by analyzing this data. The behavioral achievement concerns behaviors which the subject person 4 actually performed to improve lifestyle, and high behavioral achievement refers to the sufficient effort to improve lifestyle (in other words, lifestyle is good), and low behavioral achievement refers to sufficient that was not made to improve lifestyle (in other words, lifestyle is not good). The state index to indicate the level of behavioral achievement (called "behavioral state index") can be designed in accordance with the type of the lifestyle-related information to be used, the purpose of the type classification and the like.

The indexes that can be extracted from the measurement data are, for example, the weight difference between morning and night, consumed calories per day, meal time, number of steps, exercise intensity, walking distance, walking time, sleeping efficiency, sleeping hours, and target behavior execution rate. The index value may be a value in one measurement data, or an average value in a plurality of times of measurement data (e.g. measurement data in most recent 7 days). A dispersion (e.g. standard deviation) or a change amount in a plurality of the times of measurement data may be used as the index value. In this case, it is preferable to consider the days of the week and time zones. For example, behavior on holidays may be evaluated with a higher weight by determining a weighted average with assigning a higher weight to holidays than to weekdays. Further, the evaluation may be sub-divided by using only the measurement data in a specified time zone, or the measurement data on a specific day of the week, for calculating the index calculation.

If a questionnaire inquiring about the behavioral achievement of the subject person 4 has been filled out, as mentioned above, the behavioral state evaluating unit 12 may determine the behavioral state index value based on the response data of the questionnaire. Needless to say, a plurality of indices may be combined, or an index determined based on the response data of the questionnaire and an index determined from measurement data may be combined. In this case, the value of the behavioral state index may be calculated from a plurality of indices using an operation to determine an average, a sum total, a weighted average, a weighted sum or the like, and a function. For example, if the behavioral state index value LS on exercise is calculated using a function $f$ of a walking distance in a day, exercise intensity and walking time, as in LS=$f$ (walking distance, exercise intensity, walking time) then the level of the behavioral achievement of the subject person 4 can be evaluated accurately.

Then in step S12, the type determining unit 13 compares the psychological state index value ES acquired in step S10 with a threshold TH1, and determines as "psychological state: HIGH" if ES≥TH1, as "psychological state: LOW" if ES<TH1. Further, the type determining unit 13 compares the behavioral state index value LS acquired in step S11 with a threshold TH2, and determines as "behavioral state: HIGH" if LS≥TH2, and as "behavioral state: LOW" if LS<TH2. Then the type determining unit 13 determines which one, type 1 to type 4, that the subject person 4 corresponds to, based on the combination of the HIGH/LOW of the psychological state and the HIGH/LOW of the behavioral state.

The thresholds TH1 and TH2 may be determined based on the result of the experiments of the examinees, or may be determined from static data, such as based on an average Japanese or average user of this system. For example, if a number of steps is used as the behavioral state index, then the average number of steps of a Japanese, that is, "man: 7100 steps; woman: 6300 steps" (the result of National Health and Nutrition Examination Survey, 2012) may be used as the threshold TH2. The threshold TH2 may be changed depending on each attribute, since the exercise amount and the basal metabolism are different depending on gender, age, occupation, physical constitution and the like.

The type of working on the lifestyle improvement can be determined for the subject person 4 by the above processing. The determined type is registered in the subject person data storing unit 16. The type determining processing in FIG. 4 may be performed only once, but may preferably be performed periodically during the period of executing the lifestyle improvement program. This is because the psychological state (self-efficacy) and the behavioral state can change during the execution of the program.

The information providing control unit 14 may present the type of the subject person 4 when necessary (step S13). By notifying their type, the subject person 4 can have the opportunity to recognize and be aware of their way of working on the lifestyle improvement. Knowing the type of the subject person 4 can also help such health care providers as a physician and public health nurse to provide efficient and effective health guidance.

FIG. 5A to FIG. 5D are examples of the type confirming screens displayed on the screen of the terminal device 2. FIG. 5A is a display example when a value of the subject person 4 (star mark) is plotted on a two axes matrix of the psychological state index and the behavioral state index. In the display examples in FIG. 5A to FIG. 5C, the psychological state index is denoted by "SE", and the behavioral state index is denoted by "behavior". By the position of the plotted point, the type of subject person 4 can be quickly recognized. FIG. 5B is a display example when the time-based changes in the value of the subject person 4 are plotted on the two axes matrix. It can be observed that the subject person 4 who was initially type 4 changes to type 3 and to type 1. This type of display enables seeing the change in the attitude of the subject person 4 at a glance, hence a positive change motivates the subject person 4 to make further improvement, and a negative change provides awareness (self-examination) to the subject person 4. FIG. 5C is an example when the values of the subject person 4 are plotted on a six axes radar chart. In this example, lifestyle is divided into dietary habits, exercise habits and sleep habits, using six state indices (psychological state and behavioral state of diet, psychological state and behavioral state of exercise, and psychological state and behavioral state of sleep). The center of each axis is the threshold (neutral), and the outside thereof indicates "HIGH" and the inside thereof indicates "LOW". FIG. 5D is an example of displaying the type of the subject person 4 by text.

(5) Information Providing Control Matching the Type of Subject Person

The support information providing control matching the type of the subject person 4 will be described next. The information providing control unit 14 has a function to transmit the support information (messages) to each subject person (person executing the lifestyle improvement program) in accordance with the lifestyle improvement state of the subject person. A frequency, a number of times and a timing of providing the support information are predetermined. However, if the frequency of providing information is defined in the information source priority table (see FIG. 3B), this frequency is used. In the case of FIG. 3B, information is provided mostly to type 2 and type 4 subject persons, information is provided less to type 3 subject persons, and information is provided least to type 1 subject persons. The messages which are provided as the support information are registered in the message storing unit 15 in advance.

FIG. 6 is an example of a message table registered in the message storing unit 15. In this table, the determination logic (rules) of the lifestyle improvement state, the type of information source and the message are corresponded. For example, rule 1 is a rule that is selected when the number of continuous weeks when the target number of steps was achieved is th-weeks or more, the type of the information source is achievement experience, and the provided message is "Mr. O cleared the target number of steps continuously for th-weeks! Keep it up, and improve the record!". In FIG. 6, only four rules are listed as an example, but in an actual message table, several tens to several hundred rules are set.

Figure 7:
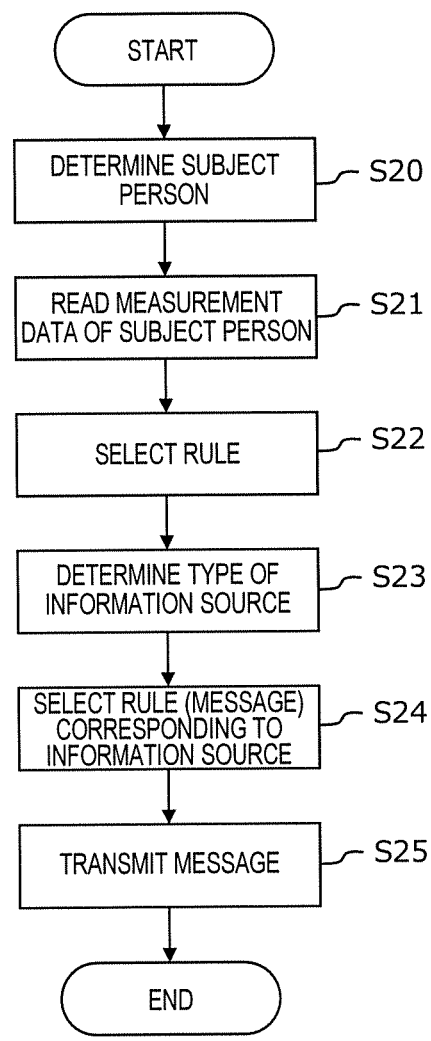
FIG. 7 is a flow chart of the information providing control.
Figure 8A:
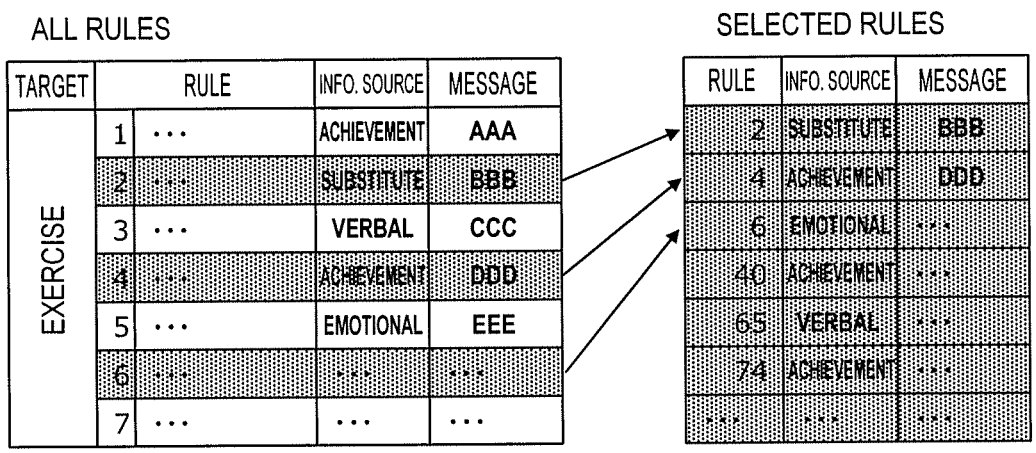
FIG. 8A and FIG. 8B are schematic diagrams depicting processing operations to extract messages to provide to the subject person from the message table.

The operation of the information providing control unit 14 will be described with reference to the flow chart in FIG. 7. First the information providing control unit 14 specifies a subject person 4 to which a message is sent (step S20), and reads the measurement data of the subject person 4 from the subject person data storing unit 16 (step S21). Then the information providing control unit 14 refers to the message table, and selects a rule corresponding to the measurement data of the subject person 4 (step S22). FIG. 8A is an example when the rules 2, 4, 6, 40, 65, 74 . . . are selected from the message table.

The information providing control unit 14 determines the type of the information source to be provided to the subject person 4 (step S23). At this time, the information providing control unit 14 determines the type of the information source to provide in accordance with probability, based on the priority levels defined in the information source priority table (see FIG. 3B). For example, if the type of subject person 4 is type 1, achievement experience is selected with a 0.5 probability, the substitute experience and the verbal persuasion are selected with a 0.2 probability, and the physiological/emotional uplift is selected with a 0.1 probability. By using the table and the selection logic in this way, priority levels can easily be controlled in accordance with the type. Further, the information source to be selected is determined based on probability, hence it can be prevented that the same type of information sources are selected at a high ratio. The description will continue based on the assumption that here achievement experience was selected.

Figure 8B:
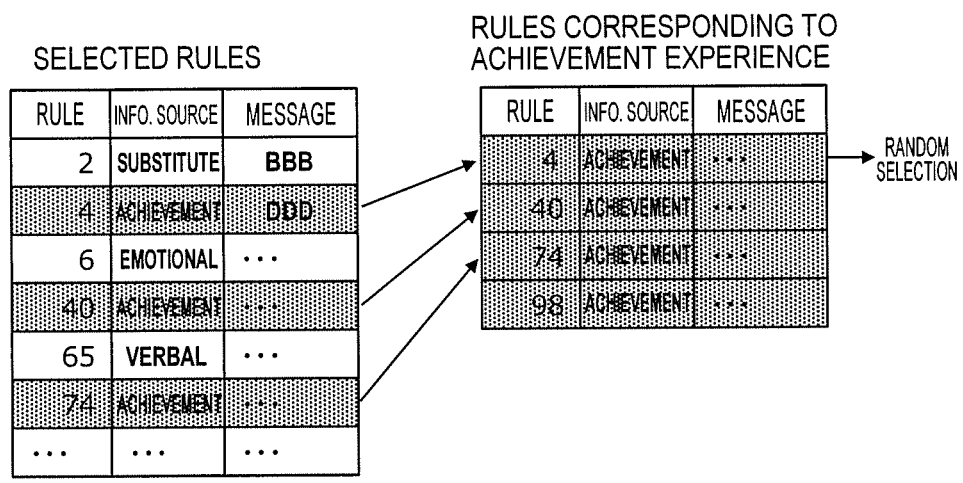

Then the information providing control unit 14 extracts only a rule (message) corresponding to the information source determined in step S23, out of the rules selected in step S22 (step S24). If a plurality of rules are extracted, the information providing control unit 14 selects one rule at random, out of the plurality of rules. Whether a message was transmitted in the past and a number of times of a transmission may be added as conditions. FIG. 8B is an example when the rules 4, 40, 74 and 98, corresponding to achievement experience, are extracted from the rules selected in step S22, then rule 4 is selected at random out of these rules.

Finally, the information providing control unit 14 transmits the message corresponding to the rule selected in step S24 to the terminal device 2 of the subject person 4 (step S25). The message may be transmitted as an email, or may be displayed on an application of the terminal device 2, or may be displayed on a browser web page of the terminal device 2. By this information providing control, the type of the information source that is provided with priority can be controlled in accordance with the type of the subject person 4.

(Advantage of this Embodiment)

According to the configuration of this embodiment described above, the type of the subject person 4, in terms of working on the lifestyle improvement, can be determined based on the psychological state (level of self-efficacy) and the behavioral state (level of behavioral achievement) of the subject person 4, so as to provide support information matching the type of the subject person 4. Therefore compared with the conventional methods which consider only the psychological state, support information that matches the personality and the behavioral characteristics of the subject person 4 more so can be provided. Further, an information source matching the type of the subject person 4 is provided with priority, hence the self-efficacy of the subject person 4 can be improved effectively, and a behavioral change to improve lifestyle and continuation of the changed behavior can be promoted.

(Modification)

In the above embodiment, the fixed information source priority table (FIG. 3B) is used. In many cases, this method can select an appropriate information source, but the selected information source may not work effectively depending on the person. Therefore as a modification, a method of personally optimizing the priority levels of the information sources by learning the response results of the subject person 4 will be described.

The information providing control unit 14 provides such a response acquisition button as "I like it!/Not so sure", and prompt the subject person 4 to input a response when the message is displayed on the terminal device 2. FIG. 9 shows examples of the messages corresponding to the four information sources, and examples of response acquiring buttons. The information providing control unit 14 determines a response as positive (in other words, that this information source is effective for the subject person 4) if such a positive reply as "I like it!", "OK!" or "Yes!" is received. If, on the other hand, such a negative reply as "Not so sure" is received, or if no response is received from the subject person 4, the information providing control unit 14 determines this as a negative response (in other words, this information source was not effective for the subject person 4). Each time a message is outputted, the information providing control unit 14 acquires the response of the subject person 4 from the terminal device 2, and records the response result in the subject person data storing unit 16.

When a certain amount of response results is stored, the information providing control unit 14 calculates and records the ratio of the messages, for which positive responses were received, with respect to the total number of provided messages (response rate) for each type of information source. FIG. 10 shows the default information source priority table for the type 1 subject person 4, and the response rate recorded for each information source. In this example, the response rates of achievement experience and verbal persuasion are very high, and the response rates of substitute experience and physiological/emotional uplift are relatively low.

Based on the response rate, the information providing control unit 14 updates the priority of each information source. For example, the priority level can be updated using the following transformation formula.

Updated priority level=default priority level+(response rate−average of response rates of four information sources)×coefficient The coefficient is a parameter to control the degree of changes, and can be freely set. The lowest row of the table in FIG. 10 shows the changed priority levels when the coefficient is set to 0.1. This operation adjusts the relative priority levels among the four information sources, so that the priority level of the information source, of which the response rate is relatively high (achievement experience and verbal persuasion in the case of FIG. 10), increases, and the priority level of the information source, of which response rate is relatively low, decreases.

According to this configuration, the types of information sources to which the subject person 4 positively responded (in other words, the influence on improving self-efficacy of the subject person 4 is large) can be learned, and the ratio of providing messages corresponding to this information source can be increased automatically. As a result, a more effective support information can be provided. Further, a structure to change the configuration or the content of the message may be provided for the information source, to which the response rate is low. For example, if the content of the message corresponding to the information source to which response rate is low is changed to a content that is personally suitable for the subject person, then self-efficacy can be effectively improved.

(Other)

The above mentioned configuration of this embodiment is merely an example of the present invention, and is not intended to limit the scope of the invention. The present invention can be carried out by various configurations within a scope of the technical concept thereof.

For example, in the above embodiment, the two indices (the psychological state index and the behavioral state index) are used as the state index to evaluate the state of the subject person in terms of lifestyle improvement, but other state indices may be used. For example, an index related to social factors (e.g. occupation, income, residential area) of the subject person, or an index related to physical factors (e.g. diseases, disabilities) of the subject person may be used as the state index. Any state index may be used, but it is preferable to evaluate the state of the subject person by multi-axial classification using a plurality of different state indices, in order to accurately understand the type of the subject person. The type classification, the information source priority table, the message table and the like are merely examples, and are not intended to limit the invention.

What is claimed is:

1. A lifestyle management supporting apparatus for providing support information to support lifestyle improvement of a subject person, the apparatus comprising:
    a lifestyle-related information acquiring unit configured to acquire lifestyle-related information which is related to the lifestyle of the subject person;
    a psychological state evaluating unit configured to determine a value of a psychological state index which indicates a level of self-efficacy for the lifestyle improvement, based on the lifestyle-related information of the subject person;
    a behavioral state evaluating unit configured to determine a value of a behavioral state index which indicates a level of behavioral achievement for the lifestyle improvement, based on the lifestyle-related information of the subject person;
    a type determining unit configured to determine a type of the subject person, based on the value of the psychological state index and the value of the behavioral state index of the subject person by using a classification by a plurality of axes of indices including the psychological state index and the behavioral state index;
    a message storing unit configured to store in advance a plurality of messages, which respectively correspond to a plurality of information sources that influence self-efficacy; and
    an information providing control unit configured to provide support information matching the type of the subject person to a terminal device of the subject person,
    wherein the type determining unit classifies the subject person into one of a plurality of types including: type 1 having high self-efficacy and high behavioral achievement; type 2 having low self-efficacy and high behavioral achievement; type 3 having high self-efficacy and low behavioral achievement; and type 4 having low self-efficacy and low behavioral achievement, by using a plurality of axes of indexes including the psychological state index and the behavioral state index,
    wherein the information providing control unit has a table in which relative priority levels among the plurality of information sources are defined for each type, and a function to provide a message, which is read from the message storing unit, as the support information, and when a message to provide to the subject person is selected from the plurality of messages, the information providing control unit selects an information source based on a probability in accordance with the relative priority level corresponding to the type of the subject person, and then selects a message corresponding to the selected information source, and
    wherein the information providing control unit is further configured to:
        display a button together with the message on the terminal device to cause the subject person to input a response to the message;
        acquire a response from the subject person inputted by the button;
        record for each information source a response rate, which is a ratio of the messages of which response from the subject person is positive, with respect to the total number of messages provided to the subject person; and
        change the relative priority levels among the four information sources, based on the response rate of each information source, so that the priority level of an information source having a relative high response rate becomes high.

2. The lifestyle management supporting apparatus according to claim 1, wherein the message storing unit stores in advance a plurality of messages, which respectively correspond to achievement experience, substitute experience, verbal persuasion, and physiological/emotional uplift, which are four information sources that influence self-efficacy.

3. The lifestyle management supporting apparatus according to claim 1, wherein the information providing control unit:
    selects a message corresponding to the achievement experience with priority over messages corresponding to other information sources when the subject person is type 1,
    selects a message corresponding to the achievement experience and a message corresponding to the verbal persuasion with priority over messages corresponding to other information sources when the subject person is type 2,
    selects a message corresponding to the substitute experience and a message corresponding to the physiological/emotional uplift with priority over messages corresponding to other information sources when the subject person is type 3, and
    selects a message corresponding to the achievement experience and a message corresponding to the substitute experience with priority over messages corresponding to other information sources when the subject person is type 4.

4. The lifestyle management supporting apparatus according to claim 1, wherein the information providing control unit changes frequency of providing the support information to the subject person, depending on the type of the subject person.

5. The lifestyle management supporting apparatus according to claim 1, wherein the information providing control unit has a function to present, as the support information, the type of the subject person determined by the type determining unit.

6. The lifestyle management supporting apparatus according to claim 1, wherein the lifestyle-related information includes response data to a questionnaire on lifestyle filled out by the subject person.

7. The lifestyle management supporting apparatus according to claim 1, wherein the lifestyle-related information includes measurement data which is acquired by measuring behavior or biological information on the subject person.

8. A lifestyle management supporting method for providing support information to support lifestyle improvement of a subject person, the method comprising:
   a step in which a computer acquires lifestyle-related information which is related to the lifestyle of the subject person;
   a step in which the computer determines a value of a psychological state index which indicates a level of self-efficacy for the lifestyle improvement, based on the lifestyle-related information of the subject person;
   a step in which the computer determines a value of a behavioral state index which indicates a level of behavioral achievement for the lifestyle improvement, based on the lifestyle-related information of the subject person;
   a step in which the computer determines a type of the subject person, based on the value of the psychological state index and the value of the behavioral state index of the subject person by using a classification by a plurality axes of indices including the psychological state index and the behavioral state index;
   a step in which the computer selects a message to be provided to the subject person from a message storing unit configured to store in advance a plurality of messages, which respectively correspond to a plurality of information sources that influence self-efficacy; and
   a step in which the computer provides support information including the selected message to a terminal device of the subject person, wherein in the step of determining the type of the subject person, the subject person is classified into one of a plurality of types including: type 1 having high self-efficacy and high behavioral achievement; type 2 having low self-efficacy and high behavioral achievement; type 3 having high self-efficacy and low behavioral achievement; and type 4 having low self-efficacy and low behavioral achievement, by using a plurality of axes of indexes including the psychological state index and the behavioral state index, wherein an information source is selected based on a probability in accordance with the relative priority level corresponding to the type of the subject person by referring to a table in which relative priority levels among the plurality of information sources are defined for each type, and then a message corresponding to the selected information source is changed selected when a message to be provided to the subject person is selected from the plurality of messages, and wherein the computer:
   displays a button together with the message on the terminal device to cause the subject person to input a response to the message;
   acquires a response from the subject person inputted by the button;
   records for each information source a response rate, which is a ratio of the messages of which response from the subject person is positive, with respect to the total number of messages provided to the subject person; and
   changes the relative priority levels among the four information sources, based on the response rate of each information source, so that the priority level of an information source having a relative high response rate becomes high.

9. A non-transitory computer readable medium that stores a program causing a computer to execute each step of the lifestyle management supporting method according to claim 8.

* * * * *